United States Patent
Kracke et al.

(10) Patent No.: US 12,168,652 B2
(45) Date of Patent: Dec. 17, 2024

(54) NEUROMUSCULAR BLOCKING AGENTS

(71) Applicant: The Curators of the University of Missouri, Columbia, MO (US)

(72) Inventors: George R. Kracke, Columbia, MO (US); Lalit N. Goswami, Columbia, MO (US); Marion F Hawthorne, Columbia, MO (US); Satish S. Jalisatgi, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 7 days.

(21) Appl. No.: 15/733,705

(22) PCT Filed: Mar. 27, 2019

(86) PCT No.: PCT/US2019/024386
§ 371 (c)(1),
(2) Date: Sep. 30, 2020

(87) PCT Pub. No.: WO2019/191301
PCT Pub. Date: Oct. 3, 2019

(65) Prior Publication Data
US 2021/0047289 A1    Feb. 18, 2021

Related U.S. Application Data

(60) Provisional application No. 62/650,702, filed on Mar. 30, 2018.

(51) Int. Cl.
*C07D 401/08* (2006.01)
*A61P 21/00* (2006.01)
*C07C 211/63* (2006.01)

(52) U.S. Cl.
CPC ............ *C07D 401/08* (2013.01); *A61P 21/00* (2018.01); *C07C 211/63* (2013.01)

(58) Field of Classification Search
None
See application file for complete search history.

(56) References Cited

PUBLICATIONS

Valliant et al (Coordination Chem Rev 232:173-230, 2002) (Year: 2002).*
CAS RN 206132-79-8 (entered into STN on May 31, 1998) (Year: 1998).*
CAS RN 206347-22-0 (entered into STN on Jun. 4, 1998) (Year: 1998).*
CAS RN 355151-96-1 (entered into STN on Sep. 7, 2001) (Year: 2001).*
CAS RN 141120-03-8 (entered into STN on May 8, 1992) (Year: 1992).*
CAS RN 28065-46-5 (entered into STN on Nov. 16, 1984) (Year: 1984).*
King et al (Inorganic Chem 25:4309-4311, 1986) (Year: 1986).*
CAS RN 1291103-30-4 (entered into STN on May 6, 2011) (Year: 2011).*

* cited by examiner

*Primary Examiner* — Craig D Ricci
(74) *Attorney, Agent, or Firm* — Sandberg Phoenix & von Gontard, PC; Tracey S. Truitt

(57) ABSTRACT

Disclosed herein are carborane derivatives of Formula I or Formula V, or a pharmaceutically acceptable salt thereof, for use as neuromuscular blocking agents. The carborane is substituted with two cationic functional groups selected from amines that form ammonium cations, ethers and/or alcohols that form oxonium cations, sulfides and/or thiols that form sulfonium cations, and phosphanes and/or phosphines that form phosphonium cations.

2 Claims, 11 Drawing Sheets a) n-BuLi, trimethylene oxide, THF, -78°C
b) MsCl, NEt₃, DCM, 0°C
c) NaI/Acetone, reflux
d) NEt₃, DMA, ACN, 0°C
e) MeI/Acetone, 0°C a) n-BuLi, trimethylene oxide, THF, -78°C
b) MsCl, NEt$_3$, DCM, 0°C
c) NaI/Acetone, reflux
d) NEt$_3$, DMA, ACN, 0°C
e) MeI/Acetone, 0°C a) n-BuLi, trimethylene oxide, THF, -78°C
b) MsCl, NEt$_3$, DCM, 0°C
c) NaI/Acetone, reflux
d) NEt$_3$, DMA, ACN, 0°C
e) MeI/Acetone, 0°C Formula II Formula III Formula IV Formula IIa Formula IIIa Formula IVa Formula IIb Formula IIIb Formula IVb Formula IIc Formula IIIc Formula IVc Formula IId Formula IIId Formula IVd Formula IIe Formula IIIe Formula IVe

NEUROMUSCULAR BLOCKING AGENTS

BACKGROUND

The present disclosure generally relates to reagents as neuromuscular blocking agents, more specifically, to a series of compounds comprised of carborane-based structural analogues of the established neuromuscular blocker, decamethonium, and the syntheses thereof.

Neuromuscular blocking agents block nicotinic acetylcholine receptors in skeletal muscles. The nicotinic acetylcholine receptor is an integral part of the neuromuscular

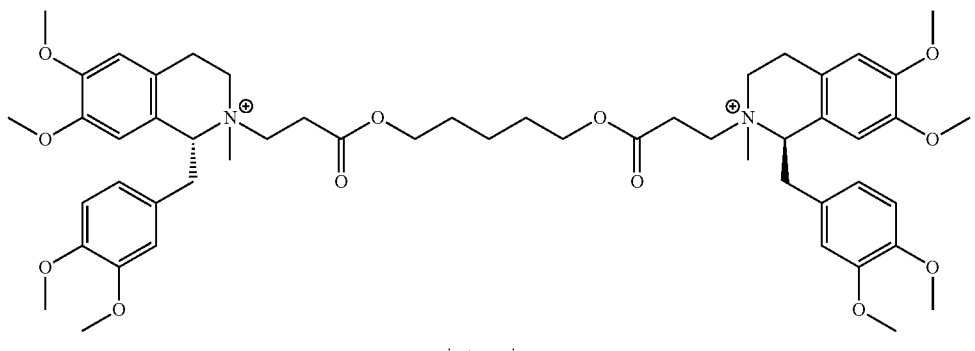

cisatracurium junction between motor nerves and skeletal muscle fibers and is involved in the initiation of skeletal muscle contraction. The junction is an important drug target for a class of pharmaceuticals called neuromuscular blocking agents, or muscle relaxants. Disruption of this junction physiology by neuromuscular blocking agents provide the basis for their therapeutic action: relaxation of skeletal muscles to prevent movement in patients during surgery and enable intubation of patients in emergency situations.

There are two functional types of neuromuscular blocking agents classified according to their mechanism of action: depolarizing and non-depolarizing. One of such neuromuscular blocking agent is decamethonium, an established depolarizing neuromuscular blocking drug that is not currently used clinically. Decamethonium, shown below, was used intravenously in patients undergoing general anesthesia to prevent spontaneous movement during surgery.

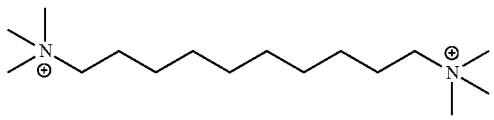

trimethyl-(10-trimethylammoniumdecyl)ammonium

Decamethonium is known to cause cardiovascular as well as pulmonary difficulties in some patients. Because of its extreme potency, it must be used only under carefully controlled circumstances. Another depolarizing neuromuscular blocker, succinylcholine, can cause hyperkalemia, cardiac arrhythmias, muscle pain, and increases in intraocular and gastric pressure especially when used in patients at high doses or for a prolonged period of time. The relatively slow onset and long duration of action of the non-depolarizing neuromuscular blocking agents make them ill-suited for emergency endotracheal intubations and elective minor surgery. Their long duration of action can also lead to residual neuromuscular block after surgery which results in postoperative respiratory complications, increased recovery times in the post anesthesia care unit, and increased healthcare costs.

There are two structural classes of non-depolarizing neuromuscular blocking agents: the benzylisoquinolines (e.g., cisatracurium and turbocurarine) and steroidal (e.g., rocuronium). Cisatracurium is used to prevent muscle contraction during surgery or in intensive care units.

The concept of closo-carboranes as hydrophobic pharmacophores in biologically active molecules has been explored in recent studies. Closo-carborane derivatives of active compounds have been shown to exhibit improved binding affinity and/or activity as both antagonists and competitive agonists in range of receptor types. However, closo-carboranes, such as the $[C_2B_{10}]$-cage, have not been explored with decamethonium or any other neuromuscular blocker or muscle relaxant.

Therefore, there is a need to provide a new series of small molecule neuromuscular blocking agents with decamethonium or other neuromuscular blocking agent derivatives substituted with the carborane $[C_2B_{10}]$-cage. There is also a need to provide a synthetic method for the carborane based decamethonium analogues and carborane analogues of other neuromuscular blocking agents.

BRIEF DESCRIPTION

In one aspect, disclosed herein is a carborane compound of Formula I, or a pharmaceutically acceptable salt thereof,

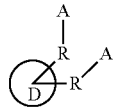

Formula I wherein D is a carborane with two carbon atoms selected from the group consisting of closo-carborane, nido-carborane, and arachno-carborane; each R is independently selected from the group consisting of $C_1$ to $C_{10}$ branched or unbranched alkyl, $C_1$ to $C_{10}$ branched or unbranched alkenyl, $C_1$ to $C_{10}$ branched or unbranched alkynyl, branched or unbranched acyl, branched or unbranched monocyclic or bicyclic aryl, and branched or unbranched monocyclic or bicyclic heteroaryl; each A is independently selected from a cationic functional group, and at least one counter-ion is present for the cationic functional group.

In another aspect, disclosed herein is a method for blocking nicotinic acetylcholine receptors in a patient in need thereof. The method generally comprises: contacting the patient with a compound of Formula I as disclosed elsewhere herein to the patient thereby blocking the nicotinic acetylcholine receptors in the patient.

In another aspect, disclosed herein is a method for inducing at least partial muscle paralysis in a patient in need thereof. The method generally comprises: administering to the patient a compound of Formula I as disclosed elsewhere herein to the patient thereby inducing at least partial muscle paralysis.

In another aspect, disclosed herein is a carborane compound of Formula V, or a pharmaceutically acceptable salt thereof,

Formula V wherein D is a carborane with two carbon atoms selected from the group consisting of closo-carborane, nido-carborane, and arachno-carborane; each R is independently selected from the group consisting of $C_1$ to $C_{10}$ branched or unbranched alkyl, $C_1$ to $C_{10}$ branched or unbranched alkenyl, $C_1$ to $C_{10}$ branched or unbranched alkynyl, branched or unbranched acyl, branched or unbranched monocyclic or bicyclic aryl, and branched or unbranched monocyclic or bicyclic heteroaryl; and Cy is a cyclic group independently selected from the group consisting of substituted or unsubstituted aryl, substituted or unsubstituted heteroaryl, substituted or unsubstituted carbocyclic and substituted or unsubstituted heterocyclic.

In another aspect, disclosed herein is a method for blocking nicotinic acetylcholine receptors in a patient in need thereof. The method generally comprises: contacting the patient with a compound of Formula V as disclosed elsewhere herein to the patient thereby blocking the nicotinic acetylcholine receptors in the patient.

In another aspect, disclosed herein is a method for inducing at least partial muscle paralysis in a patient in need thereof. The method generally comprises: administering to the patient a compound of Formula V as disclosed elsewhere herein to the patient thereby inducing at least partial muscle paralysis.

BRIEF DESCRIPTION OF THE DRAWINGS

FIG. 1 illustrates the general structure of several representative carboranes.

FIG. 2 illustrates the synthesis of compound 1.

FIG. 3 illustrates the synthesis of compound 2.

FIG. 4 illustrates the synthesis of compound 3.

FIG. 5 illustrates the mouse grip strength as a function of time after injection of mice with several representative carboranes compared to control compounds. It shows that carborane neuromuscular blocking agents and control agents cause muscle weakness as measured by loss of grip strength after injection of the agents at time zero and that strength recovers minutes later.

FIG. 6 illustrates the dose response relationships for loss of mouse grip strength as a function of dose injected for several representative carboranes compared to control compounds. Experiments were performed as in FIG. 5 and show that among the carboranes compound 3 is more potent than compound 1. The potency of the carborane agents is compared to control neuromuscular blocking agents (lower panel).

FIG. 7 illustrates the dose response relationships for loss of mouse muscle strength as a function of dose injected. Strength was measured as the areas under the curve (AUC) in the inverted screen test for three carborane neuromuscular blocking agents. These results corroborate the potency results in FIG. 6 using an independent test of muscle strength.

FIG. 8 illustrates the neostigmine reversibility of the loss of strength of rat muscles in vitro exposed to representative carborane and control compounds. It shows that compounds 1, 2, and 3 are non-depolarizers like rocuronium (ROC) because their effects are reversed by neostigmine (NEOSTIG). Succinylcholine (SUC) is a depolarizer and thus its effect is not reversed by neostigmine.

FIGS. 9A and 9B illustrate the results of patch-clamp studies of representative carboranes. FIG. 9A shows that compound 3 competes reversibly with acetylcholine for the adult, human muscle, nicotinic acetylcholine receptor thus demonstrating that it is a nondepolarizer. FIG. 9B is a summary graph showing that compounds 1, 2, and 3 compete with acetylcholine and are nondepolarizers.

FIG. 10 is an illustration of the chemical formula of Formula II.

FIG. 11 is an illustration of the chemical formula for Formula III.

FIG. 12 is an illustration of the chemical formula for Formula IV.

FIG. 13 is an illustration of the chemical formula for Formula IIa.

FIG. 14 is an illustration of the chemical formula for Formula IIIa.

FIG. 15 is an illustration of the chemical formula for Formula Iva.

FIG. 16 is an illustration of the chemical formula for Formula IIb.

FIG. 17 is an illustration of the chemical formula for Formula IIIb.

FIG. 18 is an illustration of the chemical formula for Formula IVb.

FIG. 19 is an illustration of the chemical formula for Formula IIc.

FIG. 20 is an illustration of the chemical formula for Formula IIIc.

FIG. 21 is an illustration of the chemical formula for Formula IVc.

FIG. 22 is an illustration of the chemical formula for Formula IId.

FIG. 23 is an illustration of the chemical formula for Formula IIId.

FIG. 24 is an illustration of the chemical formula for Formula IVd.

FIG. 25 is an illustration of the chemical formula for Formula IIe.

FIG. 26 is an illustration of the chemical formula for Formula IIe.

FIG. 27 is an illustration of the chemical formula for Formula IVe.

FIG. 28 is an illustration of an example of a chemical formula of compound 1.

DETAILED DESCRIPTION

Unless otherwise defined, all technical and scientific terms used herein have the same meaning as commonly understood by one of ordinary skill in the art to which this subject matter belongs.

Definitions

As used herein, the term "carborane" refers to the class of substituted or unsubstituted icosahedral compounds where the unsubstituted molecule has a general formula of $C_2B_{10}H_{12}$ or to carborane derivatives where one or more of the vertices is removed and/or one or more of the hydrogen atoms is replaced with a substituent as described elsewhere herein. These polyhedral compounds are classified based on the number of vertices missing from the parent polyhedral structure: "closo"—no missing vertices, "nido"—one missing vertice, "arachno"—two missing vertices. As known in the art, a missing vertice and/or one or more substituents on the structure will change the chemical formula of the molecule based on the atom or atoms missing from or substituted onto the parent structure.

Figure 1:
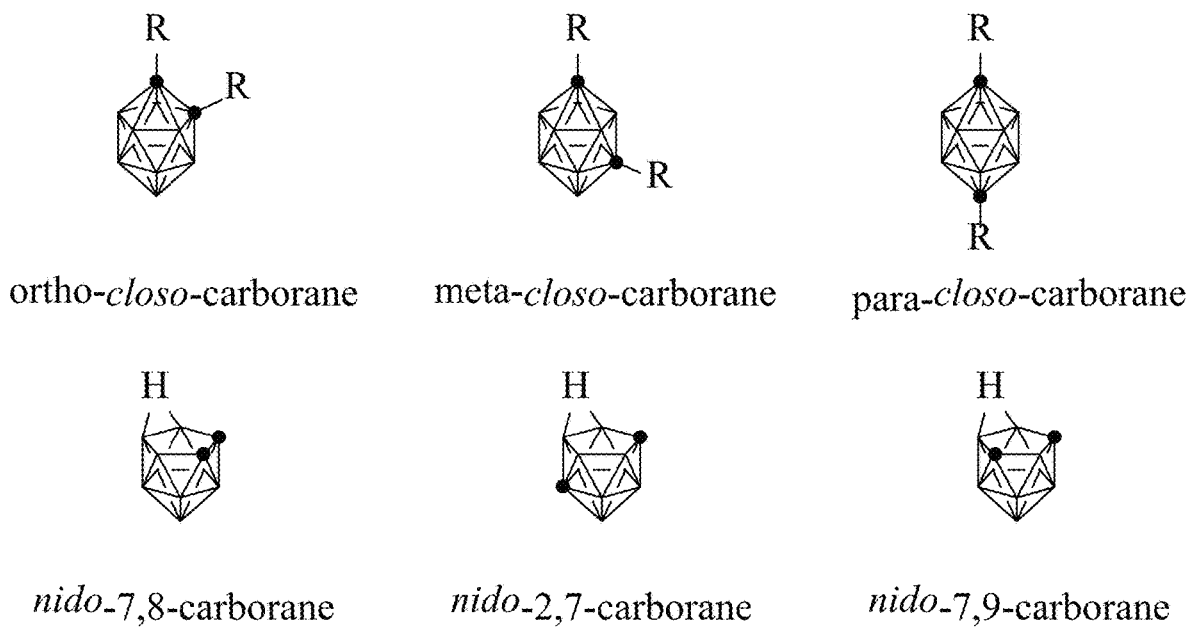

Representative carboranes are shown in FIG. 1 where the ● symbol represents the carbon atoms in the carborane derivative. Carboranes may be substituted at the carbon atom to incorporate different functionality in order to impart various properties to the molecule. Numbering in the 12 membered cage structure starts at one of the vertices and moves down one layer at a time giving the carbon atoms the lowest possible number. Hence, the "ortho" carborane is also referred to as closo-1,2-carborane. The "meta" carborane is also referred to as closo-1,7-carborane. The "para" carborane is also referred to as closo-1,12-carborane. As is common in the art, hydrogen atoms, except for the bridging hydrogens in a nido-carborane, are omitted for clarity. Due to the complexity of the structures, different, and sometimes inconsistent, nomenclature has developed for these structures. For example, "ortho" carborane has been identified in the literature as closo-1,2-carborane, closo-1,2-carbaborane and 1,2-dicarba-closo-dodecaborane. Similar nomenclature has been used for other carboranes.

Also shown in FIG. 1 are representative nido-carboranes where one boron vertice has been removed. The IUPAC name of the nido-carborane is based on the location of the two carbon atoms. Three examples are shown in FIG. 1, but other arrangements of the two carbon atoms are possible and fully encompassed herein. Numbering for nido-carboranes begins at the intact vertice and follows the same rules as for the closo-carboranes.

As used herein, the term "alkyl" means a saturated hydrocarbon, including straight or branched saturated hydrocarbon chains such as methyl ethyl, propyl, 1-methylethyl, butyl, 1-methylpropyl, 1,1-dimethylethyl, hexyl, octyl, decyl, dodecyl, and stearyl. "Cycloalkyl" groups are a subset of alkyl groups and are saturated hydrocarbon rings, such as cyclopropyl, cyclobutyl, cyclopentyl, cyclohexyl, cycloheptyl and cyclooctyl.

As used herein, the term "alkenyl" means a straight or branched hydrocarbon chain having one or more carbon-carbon double bonds, such as for example, ethene, propene, 1-butene, 2-butene, and propadiene.

As used herein, the term "alkynyl" means a straight of branched hydrocarbon chain having one or more carbon-carbon triple bonds, such as, for example, ethyne, propyne, butadiyne, and 1,4-hexadiyne.

As used herein, the term "acyl" is used herein to mean the residue of carboxylic, sulfonic or phosphorus-containing acids, for example esters, ketones, amides, alkanoyl, alkenoyl, alkynoyl, cycloalkanoyl, aralkanoyl, aroyl, carbamoyl, thiocarbamoyl, alkoxycarbonyl, sulfonyl, sulfamoyl and phosphonyl groups, in which any alkyl, alkenyl, alkynyl or aryl group may be substituted or unsubstituted.

As used herein "aryl" means an all carbon monocyclic or bicyclic aromatic hydrocarbon that is aromatic according to Huckel's Rule and has from 4 to 12 carbon atoms which may optionally be substituted with alkyl, alkenyl, alkynyl, acyl, and halo groups.

As used herein, the term "heteroaryl" means an aryl ring as defined herein where one or more of the carbon atoms is replaced by a heteroatom, such as for example, but not limited to, boron, nitrogen, oxygen, and/or sulfur. Attachment to the heteroaryl ring may be at a carbon atom or at the heteroatom if the valence of the heteroatom permits.

As used herein, the term "carbocyclic" means an all carbon unsaturated or partially saturated monocyclic or bicyclic ring having from 3 to 12 atoms which may be substituted with alkyl, alkenyl, alkynyl, acyl, and halo groups. A carbocyclic ring may optionally have one or more points of unsaturation such as a double bond in additional to additional substitution.

As used herein, the term "heterocyclic" means a saturated or partially saturated ring containing at least one heteroatom selected from nitrogen, oxygen or sulfur. The heterocyclyl ring may be monocyclic or bicyclic. Bicyclic heterocycles may have one ring aromatic while the other ring is not aromatic. A heterocyclic ring may optionally have one or more points of unsaturation such as a double bond in additional to additional substitution. Examples of heterocycle groups include, but are not limited to, pyrrolidine, piperidine, imidazolidine, pyrazolidine, butyrolactam, valerolactam, imidazolidinone, hydantoin, dioxolane, phthalimide, piperidine, 1,4-dioxane, morpholine, dihydroquinoline, tetrahydroquinoline, thiomorpholine, thiomorpholine-5-oxide, thiomorpholine-S,S-dioxide, piperazine, pyran, pyridone, 3-pyrroline, thiopyran, pyrone, tetrahydrofuran, tetrahydrothiophene, quinuclidine and the like. Attachment to the heterocyclic ring may be at a carbon atom or at the heteroatom if the valence of the heteroatom permits.

As used herein, the term "cationic functional group" means any organic functional group that is stable under physiological conditions (i.e., conditions within a human body) while supporting a positive charge. It may or may not have a positive charge in the molecule. If the functional group is neutral in the molecule, it can be used to form a positively charged species using standard organic chemistry techniques. Examples of cationic functional groups include, but are not limited to, amines that form ammonium cations, ethers and/or alcohols that form oxonium cations, sulfides and/or thiols that form sulfonium cations, and phosphanes and/or phosphines that form phosphonium cations.

Any substituted group herein may be substituted with one or more groups selected from the group consisting of alkyl, alkenyl, alkynyl, acyl, aryl, heteroaryl, halo, alkoxy, alkenyloxy, alkynyloxy, acyloxy, aryloxy, heteroaryloxy, hydroxy, nitro, mercapto, amino, substituted amino, carbamoyl, carbamoyl, thiocarbamoyl, thiocarbamoyl, cyano, and combinations thereof.

As used herein, the term "patient" means includes any warm-blooded animal including, but not limited to, dogs, cats, horses, cows, rabbits, rodents, primates, and humans. In some aspects, the patient is human. In some aspects, the patient is a dog. In some aspects, the patient is a cat. In some aspects the patient is a horse. In some aspects, the patient is a rodent.

Pharmaceutically acceptable salts are known in the art. In any aspect herein, the carborane may be in the form of a pharmaceutically acceptable salt. By way of example and not limitation, pharmaceutically acceptable salts include those as described by Berge, et al. in *J. Pharm. Sci.*, 66(1), 1 (1977), which is incorporated by reference in its entirety for all purposes. The salt may be cationic or anionic. In some embodiments, the counter ion for the pharmaceutically acceptable salt is selected from the group consisting of acetate, benzenesulfonate, benzoate, besylate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, triethiodide, adipate, alginate, aminosalicylate, anhydromethylenecitrate, arecoline, aspartate, bisulfate, butylbromide, camphorate, digluconate, dihydrobromide, disuccinate, glycerophosphate, jemisulfate, judrofluoride, judroiodide, methylenebis(salicylate), napadisylate, oxalate, pectinate, persulfate, phenylethylbarbarbiturate, picrate, propionate, thiocyanate, tosylate, undecanoate, benzathine, chloroprocaine, choline, diethanolamine, ethylenediamine, meglumine, procaine, benethamine, clemizole, diethylamine, piperazine, tromethamine, aluminum, calcium, lithium, magnesium, potassium, sodium zinc, barium and bismuth. Any functional group in the carborane capable of forming a salt may optionally form one using methods known in the art. By way of example and not limitation, amine hydrochloride salts may be formed by the addition of hydrochloric acid to the carborane. Phosphate salts may be formed by the addition of a phosphate buffer to the carborane. Any acid functionality present, such as a sulfonic acid, a carboxylic acid, or a phosphonic acid, may be deprotonated with a suitable base and a salt formed. Alternatively, an amine group may be protonated with an appropriate acid to form the amine salt. The salt form may be singly charged, doubly charged or even triply charged, and when more than one counter ion is present, each counter ion may be the same or different than each of the others.

In some aspects, the pharmaceutically acceptable salt partially or fully incorporates the cationic functional group "A" as described elsewhere herein. As one non-limiting example, the compound of Formula I includes one or two amine functional groups as the "A" group, so an ammonium salt is formed from the amine while incorporating any of the appropriately charged counter-ions as described above. In another non-limiting example, the cationic functional group is a thioether which is alkylated while incorporating any of the appropriately charged counter-ions as described above. In another non-limiting example, the "A" group is a dialkyl amine that is acylated or alkylated thereby forming the quaternary nitrogen salt while incorporating any of the appropriately charged counter-ions as described above.

In any aspect of the carborane, one or more atoms may alternatively be substituted with an isotopically labelled atom of the same element. For example, a hydrogen atom may be isotopically labelled with deuterium or tritium; a carbon atom may be isotopically labelled with $^{13}$C or $^{14}$C; a nitrogen atom may be isotopically labelled with $^{14}$N or $^{15}$N; a boron atom may be isotopically labelled with $^{10}$B or $^{11}$B. An isotopic label may be a stable isotope or may be an unstable isotope (i.e., radioactive). The carborane may contain one or more isotopic labels. The isotopic label may be partial or complete. For example, a carborane may be labeled with 50% deuterium thereby giving the molecule a signature that can be readily monitored by mass spectroscopy or other technique. As another example, the carborane may be labeled with tritium thereby giving the molecule a radioactive signature that can be monitored both in vivo and ex vivo using techniques known in the art.

The carborane can be administered by any suitable method. The method will be based on the medical needs of the patient and selected by the medical professional administering the carborane or conducting the procedure. Examples of administration methods include, but are not limited to, transdermal, oral, parenteral, subcutaneous, enteral or intravenous administration. Preferably the carborane compound will be administered using intravenous or transdermal methods. In some embodiments, the carborane is administered via a single bolus intravenous injection. In yet another embodiment, the carborane is administered by one or more bolus intravenous injections. As used herein, transcutaneous and transdermal both refer to administration through the skin of a patient and are used interchangeably.

As used herein, "enteral administration" refers to any method of administration that delivers a medicament directly or indirectly to the patient using the gastrointestinal tract. Examples of enteral administration include, but are not limited to, oral, sublingual, buccal and rectal. As used herein, "parenteral administration" refers to any method of administration that delivers a medicament directly or indirectly to the patient by injection or infusion. Examples of parenteral administration include, but are not limited to, intravenous, intraarterial, intradermal, transdermal, subcutaneous and intramuscular.

Previous studies on neuromuscular blocking agents have shown that there is an optimal distance between the cationic functional groups. In some aspects herein, the carborane is modified such that the distance between the two cationic functional groups is from 8 to 20 atoms in length or approximately 11 to 28 Å. In some aspects herein, the carborane is modified such that the distance between the two cationic functional groups is about 9 to 16 atoms in length or approximately 12 to 22 Å. In some aspects herein, the carborane is modified such that the distance between the two cationic functional groups is about 10 atoms in length or approximately 14 Å. In some aspects, the distance between the two cationic functional groups is about 10 Å, about 11 Å, about 12 Å, about 13 Å, about 14 Å, about 15 Å, about 16 Å, about 17 Å, about 18 Å, about 19 Å, about 20 Å, about 21 Å, about 22 Å, about 23 Å, about 24 Å, about 25 Å, about 26 Å, about 27 Å or about 28 Å. The distance between the two cationic functional groups is based on the two cationic atoms (e.g., the quaternary nitrogen atoms when the cationic functional groups are alkyl ammonium) in the cationic functional groups and at a local minimum of the structure as determined using computational methods known in the art. In some aspects, the distance between the two cationic functional groups is measured at the global minimum of the structure.

In one aspect, disclosed herein is a carborane compound of Formula I, or a pharmaceutically acceptable salt thereof,

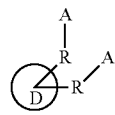

Formula I wherein D is a carborane with two carbon atoms selected from the group consisting of closo-carborane, nido-carborane, and arachno-carborane; each R is independently selected from the group consisting of $C_1$ to $C_{10}$ branched or unbranched alkyl, $C_1$ to $C_{10}$ branched or unbranched alkenyl, $C_1$ to $C_{10}$ branched or unbranched alkynyl, branched or unbranched acyl, branched or unbranched monocyclic or bicyclic aryl, and branched or unbranched monocyclic or bicyclic heteroaryl; each A is independently selected from cationic functional groups, and at least one counter-ion is present for the cationic functional groups. Each R group may be the same or different than the other. Each A group may be the same or different than the other.

Figure 10:
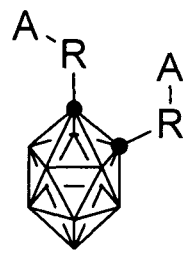
Figure 11:
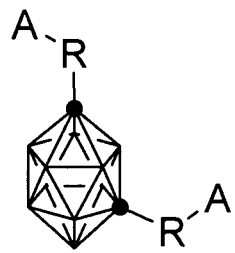
Figure 12:
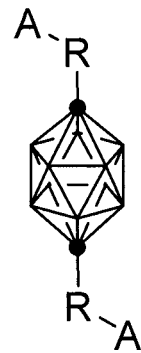

In another aspect, disclosed herein is a carborane, wherein the compound of Formula I is a closo-carborane compound of Formula II (FIG. 10), Formula III (FIG. 11) or Formula IV (FIG. 12), wherein ● is the carbon atom in the carborane.

In yet another aspect, the compound of Formula I is a compound of Formula II. In yet another aspect, the compound of Formula I is a compound of Formula III. In yet another aspect, the compound of Formula I is a compound of Formula IV.

In some aspects, each R group is a branched or unbranched $C_1$ to $C_{10}$ alkyl group. In some aspects, each cationic functional group is independently selected from the group consisting of amines, ammonium, ethers, alcohols, oxonium, sulfides, thiols, sulfonium, phosphanes, phosphines, phosphonium and combinations thereof.

Figure 13:
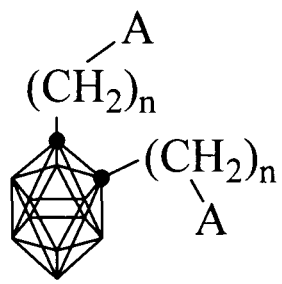
Figure 14:
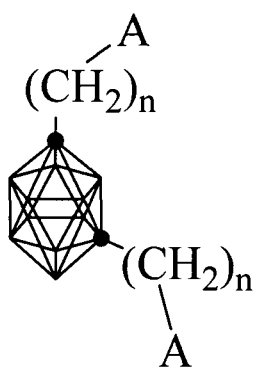
Figure 15:
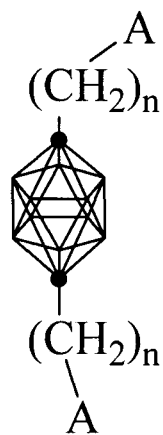

In yet another aspect, the compound of Formula I is a compound of Formula IIa (FIG. 13), Formula IIIa (FIG. 14), or Formula IVa (FIG. 15) where A is as defined elsewhere herein and where each instance of "n" is a number from 0 to 10. In some aspects, "n" is 1, 2, 3, 4, 5, 6, 7, 8, 9 or 10.

Figure 16:
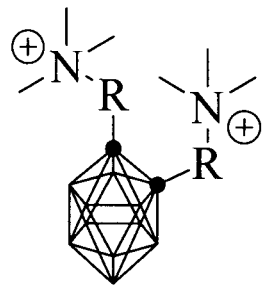
Figure 17:
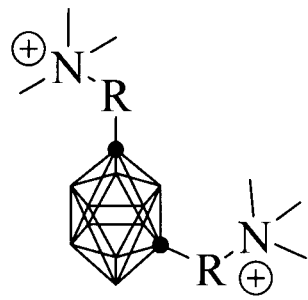
Figure 18:
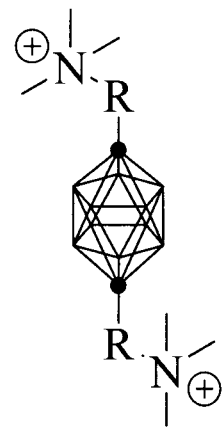

In yet another aspect, the compound of Formula I is a compound of Formula IIb (FIG. 16), Formula IIIb (FIG. 17), or Formula IVb (FIG. 18) where R is as defined elsewhere herein.

In some aspects, the cationic functional group is an alkyl ammonium group where the alkyl group is as defined elsewhere herein. In some aspects, the each alkyl group on the ammonium group is independently selected from the group consisting of methyl, ethyl, propyl, butyl, isobutyl and tert-butyl. In yet another aspect, each alkyl group is independently selected from branched or unbranched $C_1$ to $C_{10}$ alkyl groups.

In still yet another aspect, each —R-A is

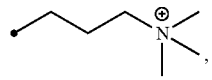

and ● is the carbon atom to which the —R-A is attached on the carborane.

In still yet another aspect, the carborane is a compound of Formula V, or a pharmaceutically acceptable salt thereof,

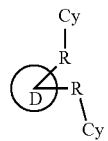

Formula V wherein D is a carborane with two carbon atoms selected from the group consisting of closo-carborane, nido-carborane, and arachno-carborane; each R is independently selected from the group consisting of $C_1$ to $C_{10}$ branched or unbranched alkyl, $C_1$ to $C_{10}$ branched or unbranched alkenyl, $C_1$ to $C_{10}$ branched or unbranched alkynyl, branched or unbranched acyl, branched or unbranched monocyclic or bicyclic aryl, and branched or unbranched monocyclic or bicyclic heteroaryl, and each Cy is a cyclic group independently selected from the group consisting of substituted or unsubstituted aryl, substituted or unsubstituted heteroaryl, substituted or unsubstituted carbocyclic, and substituted or unsubstituted heterocyclic.

Figure 19:
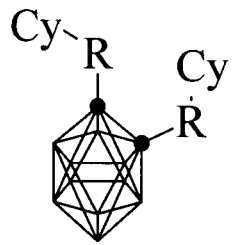
Figure 20:
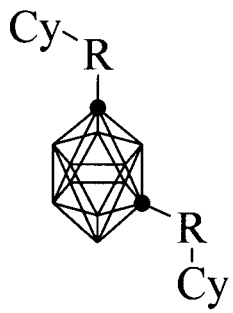
Figure 21:
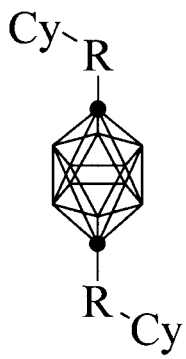

In yet another aspect, the compound of Formula V is a compound of Formula IIc (FIG. 19), Formula IIIc (FIG. 20), or Formula IVc (FIG. 21) where R and Cy are as defined elsewhere herein.

Figure 22:
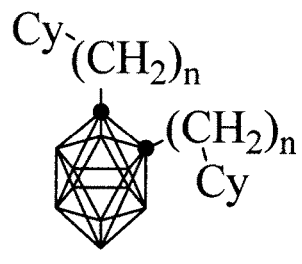
Figure 23:
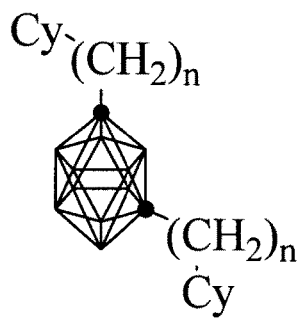
Figure 24:

In yet another aspect, the compound of Formula V is a compound of Formula IId (FIG. 22), Formula IIId (FIG. 23), or Formula IVd (FIG. 24) where Cy is as defined elsewhere herein, and where each instance of "n" is a number from 1 to 10. In some aspects, "n" is 1, 2, 3, 4, 5, 6, 7, 8, 9 or 10.

Figure 25:
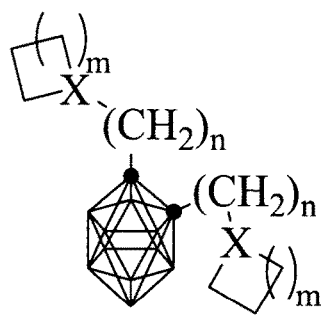
Figure 26:
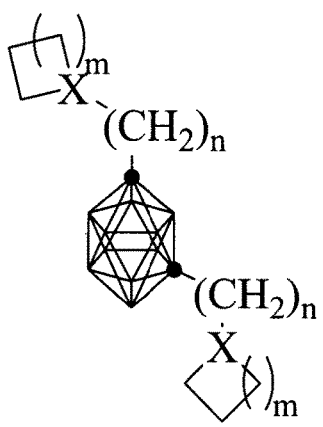
Figure 27:
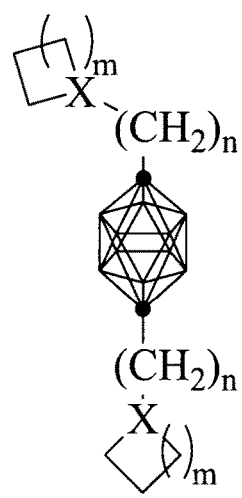

In yet another aspect, the compound of Formula V is a compound of Formula IIe (FIG. 25), Formula IIIe (FIG. 26), or IVe (FIG. 27), wherein X is a heteroatom in a monocylic or bicylic heteroaryl or heterocyclic ring, and "m" is a number from 0 to 10. In some aspects, "m" is 0, 1, 2, 3, 4, 5, 6, 7, 8, 9 or 10. In some aspects, additional heteroatoms and/or substitutions are present in each ring. In some aspects, when X is nitrogen, the nitrogen may include an additional substituent to make a quaternary salt. The quaternizing group on the nitrogen is selected from the group consisting of alkyl, alkenyl, alkynyl, acyl, aryl, heteroaryl, halo, alkoxy, alkenyloxy, alkynyloxy, acyloxy, aryloxy, heteroaryloxy, hydroxy, nitro, mercapto, amino, substituted amino, carbamoyl, carbamoyl, thiocarbamoyl, thiocarbamoyl, cyano, and combinations thereof. In some aspects, the quaternizing group is selected from the group consisting of methyl, ethyl, propyl and butyl. In some aspects, the quaternizing group is methyl.

In yet another aspect, the counter-ions are independently selected from the group consisting of acetate, bromide, camsylate, chloride, fluoride, formate, fumarate, iodide, maleate, mesylate, nitrate, oxalate, phosphate, sulfate, tartrate, thiocyanate, tosylate and combinations thereof. In some aspects, there are two halide counter-ions where each may be the same or different as the other. In still yet another aspect, the two halide counter-ions are both iodide. In still yet another aspect, the two halide counter-ions are both chloride. In still yet another aspect, the two halide counter-ions are both bromide. In still yet another aspect, the two halide counter-ions are both fluoride.

Figure 28:
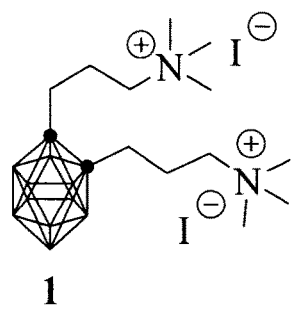
Figure 29:
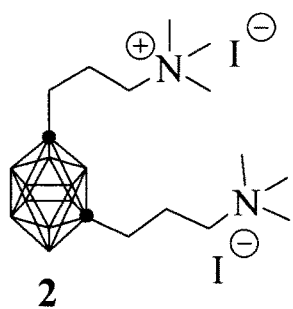
FIG. 29 is an illustration of an example of a chemical formula of compound 2.
Figure 30:
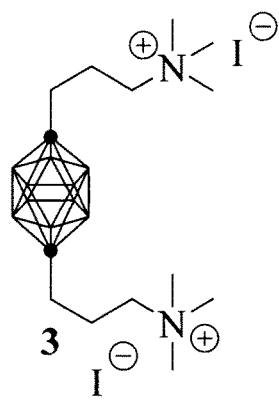
FIG. 30 is an illustration of an example of a chemical formula of compound 3.

In some aspects, the compounds of Formula I are selected from the group consisting of compound 1(FIG. 28), compound 2 (FIG. 29) and compound 3 (FIG. 30). Synthesis of these compounds is fully illustrated in the Examples below.

In some aspects, the D group carborane is a closo-carborane. In some aspects, the D group carborane is an ortho-closo-carborane. In some aspects, the D group carborane is an meta-closo-carborane. In some aspects, the D group carborane is an para-closo-carborane. In some aspects, the D group carborane is a nido-carborane. In some aspects, the D group carborane is an arachno-carborane.

Figure 31:
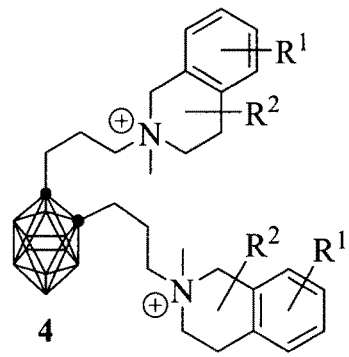
FIG. 31 is an illustration of an example of a chemical formula of compound 4.
Figure 32:
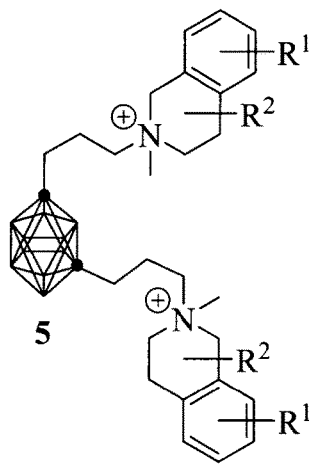
FIG. 32 is an illustration of an example of a chemical formula of compound 5.
Figure 33:
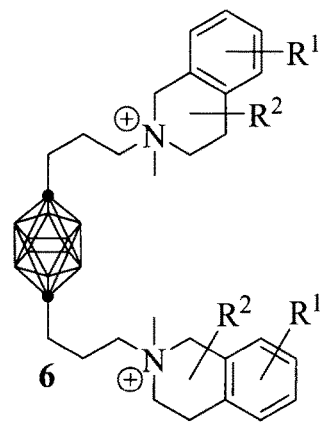
FIG. 33 is an illustration of an example of a chemical formula of compound 6.

In some aspects, the compounds of Formula V are selected from the group consisting of general compounds 4 (FIG. 31), 5 (FIG. 32), and 6 (FIG. 33), where each aromatic ring has from 0 to 4 $R^1$ groups each independently selected from the group consisting of alkyl, alkenyl, alkynyl, acyl, aryl, heteroaryl, halo, alkoxy, alkenyloxy, alkynyloxy, acyloxy, aryloxy, heteroaryloxy, hydroxy, nitro, mercapto, amino, substituted amino, carbamoyl, carbamoyl, thiocarbamoyl, thiocarbamoyl, cyano, and combinations thereof, and each heterocyclic ring has from 0 to 3 $R^2$ groups each independently selected from the group consisting of alkyl, alkenyl, alkynyl, acyl, aryl, heteroaryl, halo, alkoxy, alkenyloxy, alkynyloxy, acyloxy, aryloxy, heteroaryloxy, hydroxy, nitro, mercapto, amino, substituted amino, carbamoyl, carbamoyl, thiocarbamoyl, thiocarbamoyl, cyano, and combinations thereof. The addition of an $R^2$ group will create a chiral center, and each chiral center thus created may be R or S. In some aspects, the molecule is racemic.

In some aspects, at least one $R^1$ is present and is an alkoxy group. In some aspects, at least one $R^1$ is present on both aromatic rings and is an alkoxy group. Synthesis of these compounds is done using the same general route illustrated for compound 1 (FIG. 28), compound 2 (FIG. 29), and compound 3 (FIG. 30) respectively.

Also disclosed herein is a method for blocking nicotinic acetylcholine receptors in a patient in need thereof. The method generally comprises: contacting the patient with a compound of Formula I as described elsewhere herein.

Also disclosed herein is a method for inducing at least partial muscle paralysis in a patient in need thereof. The method generally comprises: administering to the patient a compound of Formula I as described elsewhere herein to the patient thereby inducing at least partial muscle paralysis.

For either of these methods, the compound of Formula I can be administered to the patient using any suitable method, including, but not limited to, enteral, intravenous, oral, parenteral, subcutaneous, or transdermal administration.

Also disclosed herein is a method for blocking nicotinic acetylcholine receptors in a patient in need thereof. The method generally comprises: contacting the patient with a compound of Formula V as described elsewhere herein.

Also disclosed herein is a method for inducing at least partial muscle paralysis in a patient in need thereof. The method generally comprises: administering to the patient a compound of Formula V as described elsewhere herein to the patient thereby inducing at least partial muscle paralysis.

For either of these methods, the compound of Formula V can be administered to the patient using any suitable method, including, but not limited to, enteral, intravenous, oral, parenteral, subcutaneous, or transdermal administration.

Examples

General Chemistry Experimental Details: Common reagents and chromatographic solvents were obtained from commercial suppliers (VWR International, Sigma-Aldrich, and Fisher Scientific) and used without any further purification. Water was obtained from a Barnstead NANOpure water purification system operating at 18.2 MΩ×cm. NMR spectra were recorded on Bruker Ascend-400, Bruker Avance 400 and 500 MHz spectrometers. Chemical shifts (δ, ppm) for $^1H$ and $^{13}C$ were referenced to residual solvent peaks. Boron chemical shifts were externally referenced to $BF_3 \cdot Et_2O$. High resolution mass spectra (HRMS) were acquired on Bruker Compact ESI-Q-TOF system and data reported as follows: (m/z: calculated; m/z: found). Abbreviations: ACN=Acetonitrile, MeOH=Methanol, n-BuLi=nbutyllithium, THF=Tetrahydrofuran, $Et_3N$=Triethylamine, RT=Room temperature, DCM=Dichloromethane, MsCl=Methanesulfonyl chloride, Ar=Argon, h=hour, NaI=Sodium iodide, MeI=Methyl iodide.

Figure 2:
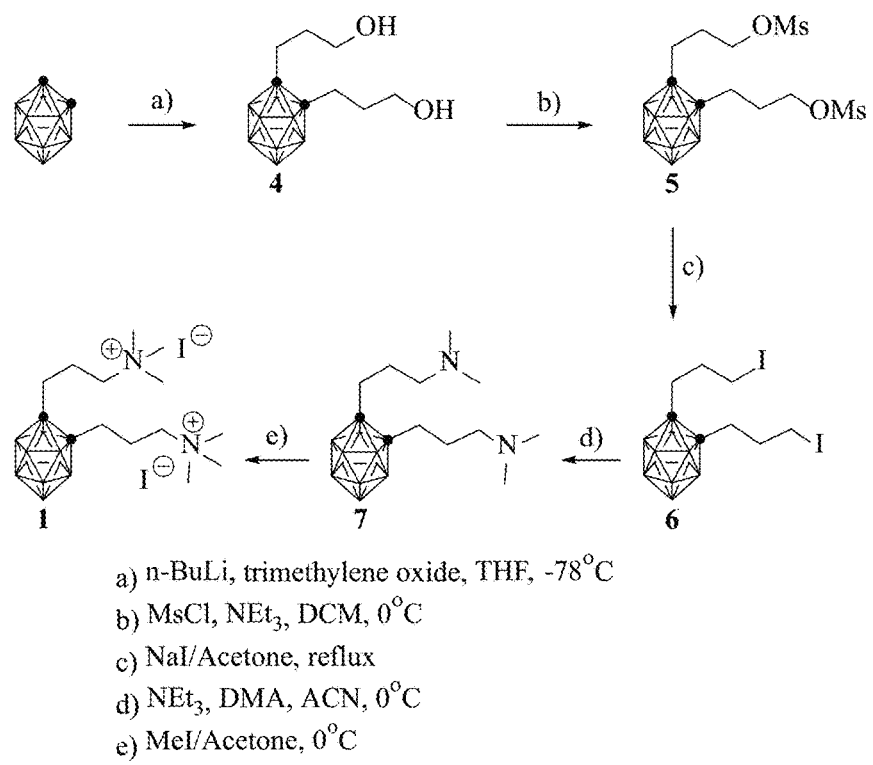

FIG. 2 illustrates the synthesis of compound 1 (also called o-NMBA), an ortho-closo-carborane.

Synthesis of 1,2-bis(propan-1-ol)-1,2-closo-carborane (4): In a 250 ml round bottom flask (RBF), ortho-[1,2-$C_2B_{10}H_{12}$] (4.00 g, 27.8 mmol) was dissolved in dry THF (100 mL) and cooled to −78° C. under an Ar(g) atmosphere, and n-BuLi (27.8 mL, 69.4 mmol, 2.5 M in hexanes) was added via syringe over 30 min. The mixture was stirred for 3 h while allowing the reaction temperature to rise up to −20° C. After 3 h, the reaction mixture was cooled again to −78° C. and trimethylene oxide (4.08 g, 69.4 mmol) was added via syringe over 30 min. The reaction mixture was slowly allowed to warm to ambient temperature and stirred for 15 h. After 15 h, the reaction mixture was cooled to −78° C. and quenched with 100 mL of 5% HCl(aq). The mixture was allowed to warm to ambient temperature and extracted with ethyl acetate (3×100 mL). The organic layers was separated, dried over anhydrous sodium sulfate ($Na_2SO_4$) and concentrated. The crude material was dissolved in a minimum amount of DCM, and the product was precipitated as a white solid by adding hexane. The white solid was filtered, washed with hexane (3×50 mL) and dried under high vacuum. Yield: 6.2 g (86%). $^1H$ NMR (500 MHz, $CD_3OD$): δ 3.56 (t, 4H, J=6.0 Hz), 2.37 (m, 4H), 1.76 (m, 4H), 2.9-1.4 (brm, 10H, B—H). $^{11}B$ NMR (160 MHz, $CD_3OD$): δ −6.56, −11.3, −12.2. $^{13}C$ NMR (125 MHz, $CD_3OD$): δ 81.5, 61.6, 33.7, 32.7. HRMS-ESI (m/z): Calcd. for $C_8H_{23}B_{10}O_2$ [M−H]⁻ 259.2976. Found 259.2701, Calcd. for $C_8H_{24}B_{10}ClO_2$ [M+Cl]⁻ 295.2468. Found 295.2318.

Synthesis of 1,2-bis(propan-3-dimethanesulfonate)-1,2-closo-carborane (5): A mixture of $Et_3N$ (4.03 g, 39.9 mmol) and 4 (2.60 g, 9.98 mmol) in DCM (30 mL) was stirred at 0° C. under an Ar(g) atmosphere, and a solution of MsCl (3.43 g, 29.9 mmol) in DCM (20 mL) was added slowly over 15 min. After the addition was complete, the reaction was allowed to warm to ambient temperature and stirred for an additional 3 h. The reaction mixture was concentrated to dryness, dissolved in DCM (100 mL), and washed with 100 mL of 5% HCl (aq) and brine. The organic layer was separated, dried over $Na_2SO_4$ and concentrated in vacuo to give the pure product as pale yellow oil. This product was used in the next step without any additional purification. Yield: 4.9 g (crude). $^1H$ NMR (500 MHz, $CDCl_3$): δ 4.32 (t, 4H, J=5.5 Hz), 3.02 (s, 6H, OMs), 2.34 (m, 4H), 1.99 (m, 4H), 2.9-1.4 (brm, 10H, B—H). $^{11}B$ NMR (160 MHz, $CDCl_3$): δ −4.04, −4.94, −9.71, −10.5. $^{13}C$ NMR (125 MHz, $CDCl_3$): δ 78.6, 68.3, 37.5, 31.1, 29.2. HRMS-ESI (m/z): Calcd. for $C_{10}H_{32}B_{10}NO_6S_2$ [M+NH₄]⁺ 434.2674. Found 434.2789. Calcd. for $Cu_{11}H_{29}B_{10}O_8S_2$ [M+HCOO]⁻ 461.2307. Found 461.2444.

Synthesis of 1,2-bis(3-iodopropyl)-1,2-closo-carborane (6): A mixture of 5 (9.98 mmol) and NaI (8.97 g, 59.9 mmol) in acetone (80 mL) was stirred for 12 h at 65° C. The reaction mixture was concentrated to dryness and filtered over celite with DCM. The filtrate was concentrated and purified by silica gel chromatography (gradient-eluent: 0-5-10-15% ethyl acetate in hexane) to obtain the product as a colorless oil. Yield: 4.3 g (89% in two steps). $^1$H NMR (500 MHz, CDCl$_3$): δ 3.19 (t, 4H, J=6.5 Hz), 2.34 (m, 4H), 2.04 (m, 4H), 2.9-1.4 (brm, 10H, B—H). $^{11}$B NMR (128 MHz, CDCl$_3$): δ −4.50, −10.1, −10.7. $^{13}$C NMR (125 MHz, CDCl$_3$): δ 78.5, 35.8, 32.6, 4.45. HRMS-ESI (m/z): Calcd. for C$_9$H$_{23}$B$_{10}$I$_2$O$_2$ [M+HCOO]$^-$ 525.0791. Found 525.1287.

Synthesis of 1,2-bis(N, N-dimethylpropan-1-amine)-1,2-closo-carborane (7): A mixture of 6 (1.30 g, 2.70 mmol) and triethylamine (1.36 g, 13.5 mmol) in acetonitrile (35 mL) was stirred at 0° C. and dimethylamine (0.61 g, 13.5 mmol, 40% water solution) was added. The reaction mixture was slowly allowed to warm to ambient temperature and stirred for 12 h and concentrated to dryness. The residue was dissolved in 100 mLs of DCM and washed with 100 mL of NaHCO$_3$(aq, sat'd). The organic layer was separated, dried over Na$_2$SO$_4$ and concentrated. The crude product was purified by column chromatography on alumina (gradient-eluent: 0-1-2-3% methanol in DCM) to obtain the product as a colorless oil. Yield: 0.8 g (93%). $^1$H NMR (500 MHz, CDCl$_3$): δ 2.25-2.19 (m, 8H), 2.17 (s, 12H, —NMe$_2$), 1.67 (m, 4H), 2.9-1.4 (brm, 10H, B—H). $^{11}$B NMR (160 MHz, CDCl$_3$): δ −4.82, −10.4. $^{13}$C NMR (125 MHz, CDCl$_3$): δ 79.8, 58.4, 45.2, 32.6, 27.7. HRMS-ESI (m/z): Calcd. for C$_{12}$H$_{35}$B$_{10}$N$_2$ [M+H]$^+$ 315.3804. Found 315.3765. Calcd. for C$_{12}$H$_{36}$B$_{10}$N$_2$ [M+2H]$^{2+}$ 158.1938. Found 158.1920.

Synthesis of 1,2-bis(N, N, N-trimethylpropan-1-aminium)-1,2-closo-carborane di-iodide (1): A mixture of 7 (0.50 g, 1.59 mmol) and acetone (20 ml) was cooled to 0° C., and MeI (0.67 g, 4.76 mmol) was slowly added. The reaction was stirred at 0° C. for 30 min, and a white precipitate formed within 15-20 min. The reaction mixture was partially concentrated and filtered. The solid white residue was washed with a 50% acetone-hexane mixture and dried under high vacuum to obtain the pure product as a white solid. Yield: 0.92 g (97%). $^1$H NMR (400 MHz, CD$_3$OD): δ 3.64 (t, 4H, J=6.0 Hz), 3.23 (s, 18H, —NMe$_3$), 2.54 (t, 4H, J=6.4 Hz), 2.04 (m, 4H), 2.9-1.4 (brm, 10H, B—H). $^{11}$B NMR (128 MHz, CD$_3$OD): δ −4.74, −10.2. $^{13}$C NMR (100 MHz, CD$_3$OD): δ 80.7, 66.0, 54.0, 32.1, 24.5. HRMS-ESI (m/z): Calcd. for C$_{14}$H$_{40}$B$_{10}$N$_2$ [M]$^{2+}$ 172.2106. Found 172.2101. Calcd. for C$_{14}$H$_{40}$B$_{10}$IN$_2$ [M+I]$^+$ 471.3252. Found 471.3247. Calcd. for C$_{15}$H$_{41}$B$_{10}$N$_2$O$_2$ [M+HCOO]$^+$ 389.4172. Found 389.4188.

Figure 3:
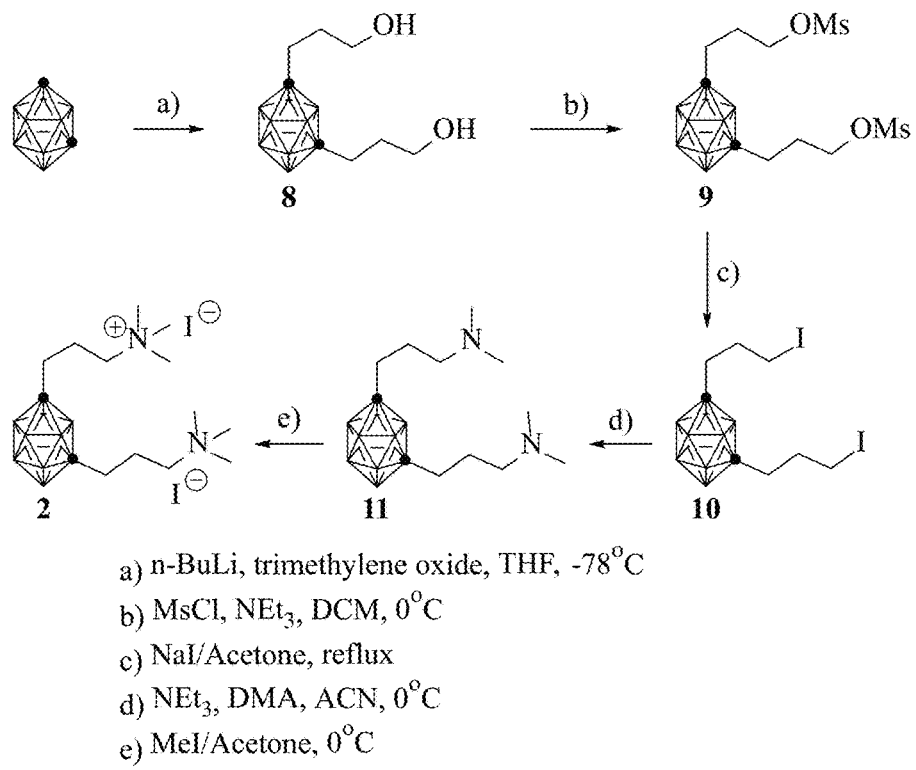

FIG. 3 illustrates the synthesis of compound 2 (also called m-NMBA), a meta-closo-carborane.

Synthesis of 1,7-bis(propan-1-ol)-1,7-closo-carborane (8): Compound 8 was prepared from meta-[1, 7-C$_2$B$_{10}$H$_{12}$] following a similar procedure described for the preparation of 4 using meta-[1,7-C$_2$B$_{10}$H$_{12}$] (2.00 g, 13.9 mmol), n-BuLi (13.9 mL, 34.7 mmol, 2.5 M in hexanes) and trimethylene oxide (2.04 g, 34.7 mmol). Yield: 3.4 g (94%). $^1$H NMR (500 MHz, CD$_3$OD): δ 3.48 (t, 4H, J=6.0 Hz), 2.07 (m, 4H), 1.59 (m, 4H), 3.2-1.4 (brm, 10H, B—H). $^{11}$B NMR (160 MHz, CD$_3$OD): δ 7.38, −11.2, −13.4. $^{13}$C NMR (125 MHz, CD$_3$OD): δ 77.2, 61.7, 34.7, 34.0. HRMS-ESI (m/z): Calcd. for C$_9$H$_{25}$B$_{10}$O$_4$ [M+HCOO]$^-$ 305.2766. Found 305.2772.

Synthesis of 1,7-bis(propan-3-dimethanesulfonate)-1,7-closo-carborane (9): Compound 9 was prepared from 8 following a similar procedure described for the preparation of 5 using 8 (2.00 g, 7.68 mmol), Et$_3$N (3.10 g, 30.7 mmol) and MsCl (2.64 g, 23.0 mmol). Yield: 3.5 g (crude). $^1$H NMR (500 MHz, CDCl$_3$): δ 4.10 (t, 4H, J=6.0 Hz), 2.97 (s, 6H, OMs), 2.04 (m, 4H), 1.77 (m, 4H), 3.2-1.4 (brm, 10H, B—H). $^{11}$B NMR (160 MHz, CDCl$_3$): δ −7.63, −11.3, −13.9. $^{13}$C NMR (125 MHz, CDCl$_3$): δ 74.6, 66.4, 37.3, 32.8, 29.3. HRMS-ESI (m/z): Calcd. for C$_{10}$H$_{28}$B$_{10}$ClO$_6$S$_2$ [M+Cl]$^-$ 452.1994. Found 452.1884. Calcd. for C$_{11}$H$_{29}$B$_{10}$O$_8$S$_2$ [M+HCOO]$^-$ 461.2308. Found 461.2197.

Synthesis of 1,7-bis(3-iodopropyl)-1,7-closo-carborane (10): Compound 10 was prepared from 9 following a similar procedure described for the preparation of 6 using a mixture of 9 (7.68 mmol) and NaI (6.90 g, 46.0 mmol). Yield: 3.5 g (95% in two steps). $^1$H NMR (500 MHz, CDCl$_3$): δ 3.07 (t, 4H, J=7.0 Hz), 2.04 (m, 4H), 1.84 (m, 4H), 3.2-1.4 (brm, 10H, B—H). $^{11}$B NMR (160 MHz, CDCl$_3$): δ −7.21, −11.1, −13.6. $^{13}$C NMR (125 MHz, CDCl$_3$): δ 74.5, 37.6, 33.1, 4.34. HRMS-ESI (m/z): Calcd. for C$_8$H$_{22}$B$_{10}$I$_2$KNa [M+Na+K]$^+$ 542.0349. Found 542.2200.

Synthesis of 1,7-bis(N, N-dimethylpropan-1-amine)-1,7-closo-carborane (11): Compound 11 was prepared from 10 following a similar procedure described for the preparation of 7 using a mixture of 10 (1.70 g, 3.54 mmol), triethylamine (1.78 g, 17.7 mmol) and dimethylamine (0.79 g, 17.7 mmol, 40% water solution). Yield: 1.0 g (90%). $^1$H NMR (500 MHz, CDCl$_3$): δ 2.12 (s, 12H, NMe$_2$), 2.10 (m, 4H), 1.91 (m, 4H), 1.46 (m, 4H), 3.2-1.4 (brm, 10H, B—H). $^{11}$B NMR (160 MHz, CDCl$_3$): δ −7.32, −11.2, −13.2. $^{13}$C NMR (125 MHz, CDCl$_3$): δ 75.7, 58.6, 45.3, 34.6, 28.0. HRMS-ESI (m/z): Calcd. for C$_{12}$H$_{36}$B$_{10}$N$_2$ [M+H]$^+$. 315.3804. Found 315.3843. Calcd. for C$_{12}$H$_{36}$B$_{10}$N$_2$ [M+2H]$^{2+}$ 158.1938. Found 158.1964.

Synthesis of 1,7-bis(N, N, N-trimethylpropan-1-aminium)-1,7-closo-carborane di-iodide (2): Compound 2 was prepared from 11 following a similar procedure described for the preparation of 1 using a mixture of 11 (0.20 g, 0.63 mmol) and MeI (0.27 g, 1.90 mmol). The product was obtained as white solid. Yield: 0.38 g (100%). $^1$H NMR (400 MHz, CD$_3$OD): δ 3.33 (m, 4H), 3.21 (s, 18H, —NMe$_3$), 2.10 (m, 4H), 1.90 (m, 4H), 3.20-1.40 (brm, 10H, B—H). $^{11}$B NMR (128 MHz, CD$_3$OD): δ −6.86, −11.0, −13.4. $^{13}$C NMR (100 MHz, CD$_3$OD): δ 76.1, 66.3, 54.0, 34.1, 24.7. HRMS-ESI (m/z): Calcd. for C$_{14}$H$_{40}$B$_{10}$N$_2$ [M]$^{2+}$ 172.2095. Found 172.2100.

Figure 4:
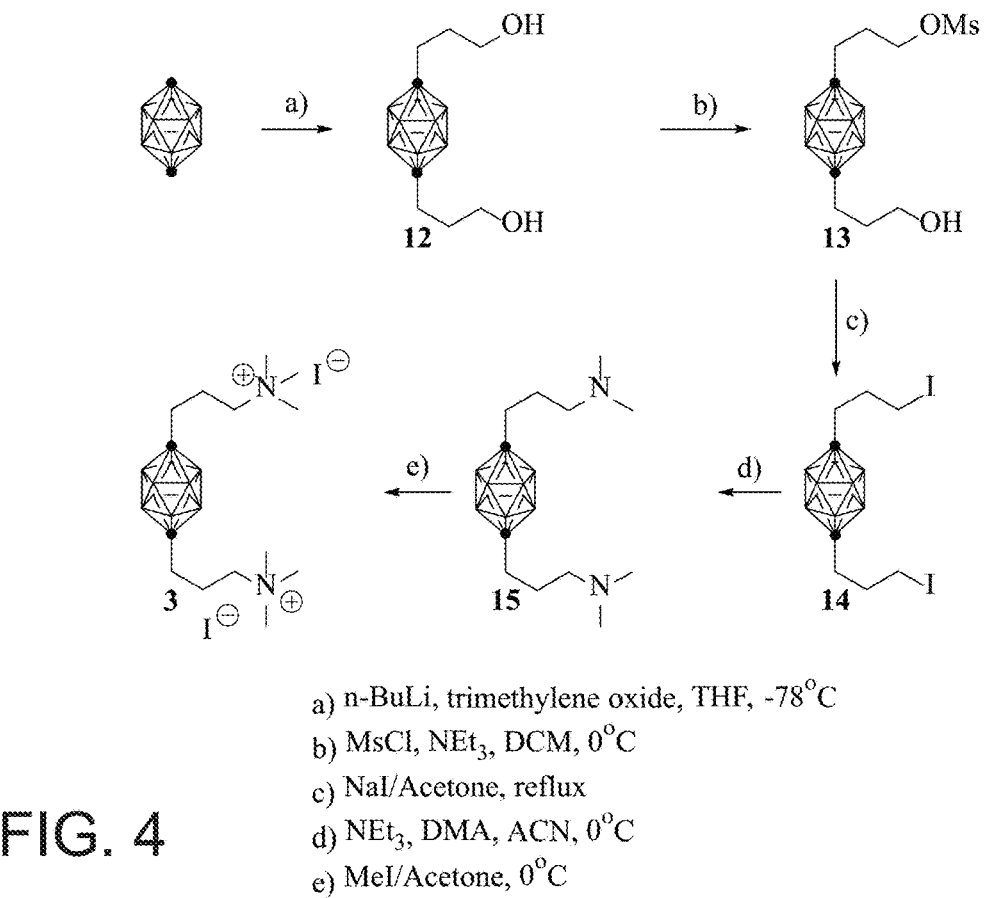

FIG. 4 illustrates the synthesis of compound 3 (also called p-NMBA), a para-closo-carborane.

Synthesis of 1,12-bis(propan-1-ol)-1,12-closo-carborane (12): Compound 12 was prepared from para-[1, 12-C$_2$B$_{10}$H$_{12}$] following a similar procedure described for the preparation of 4 from para-[1, 12-C$_2$B$_{10}$H$_{12}$] (1.00 g, 6.94 mmol), n-BuLi (6.94 mL, 17.3 mmol, 2.5 M in hexanes) and trimethylene oxide (1.02 g, 17.3 mmol). Yield: 1.7 g (94%). $^1$H NMR (500 MHz, CD$_3$OD): δ 3.38 (t, 4H, J=6.5 Hz), 1.74 (m, 4H), 1.38 (m, 4H), 2.70-1.70 (brm, 10H, B—H). $^{11}$B NMR (160 MHz, CD$_3$OD): δ −12.8. $^{13}$C NMR (125 MHz, CD$_3$OD): δ 61.8, 35.4, 33.6. HRMS-ESI (m/z): Calcd. for C$_8$H$_{23}$B$_{10}$O$_2$ [M+H]$^+$ 262.2856, Found 262.2869.

Synthesis of 1,12-bis(propan-3-dimethanesulfonate)-1, 12-closo-carborane (13): Compound 13 was prepared from 12 following a similar procedure described for the preparation of 5 using 12 (1.00 g, 3.84 mmol), Et$_3$N (1.55 g, 15.3 mmol) and MsCl (1.31 g, 11.5 mmol). Yield: 1.6 g (crude). $^1$H NMR (500 MHz, CDCl$_3$): δ 4.03 (t, 4H, J=6.0 Hz), 2.95 (s, 6H, OMs), 1.73 (m, 4H), 1.58 (m, 4H), 2.70-1.70 (brm, 10H, B—H). $^{11}$B NMR (160 MHz, CDCl$_3$): δ −12.8. $^{13}$C NMR (125 MHz, CDCl$_3$): δ 77.9, 68.4, 37.3, 33.6, 28.8. HRMS-ESI (m/z): Calcd. for C$_{10}$H$_{32}$B$_{10}$NO$_6$S$_2$ [M+NH$_4$]$^+$ 434.2674. Found 434.2701.

Synthesis of 1,12-bis(3-iodopropyl)-1,12-closo-carborane (14): Compound 14 was prepared from 13 following a similar procedure described for the preparation of 6 using a mixture of 13 (3.84 mmol) and NaI (3.45 g, 23.0 mmol). Yield: 1.6 g (87% in two steps). $^1$H NMR (500 MHz, CDCl$_3$): δ 2.97 (t, 4H, J=6.5 Hz), 1.71 (m, 4H), 1.64 (m, 4H), 2.70-1.70 (brm, 10H, B—H). $^{11}$B NMR (160 MHz, CDCl$_3$): δ −12.8. $^{13}$C NMR (125 MHz, CDCl$_3$): δ 77.9, 38.3, 32.8, 4.50. HRMS-ESI (m/z): Calcd. for C$_9$H$_{23}$B$_{10}$I$_2$O$_2$ [M+HCOO-]$^-$ 525.0801. Found 525.0814. Calcd. for C$_8$H$_{21}$B$_{10}$I$_2$ [M−H]$^-$ 479.0745. Found 479.0671.

Synthesis of 1,12-bis(N, N-dimethylpropan-1-amine)-1,12-closo-carborane (15): Compound 15 was prepared from 14 following a similar procedure described for the preparation of 7 using a mixture of 14 (1.60 g, 3.32 mmol), triethylamine (1.68 g, 16.6 mmol) and dimethylamine (0.75 g, 16.6 mmol, 40% water solution). Yield: 0.9 g (86%). $^1$H NMR (400 MHz, CDCl$_3$): δ 2.08 (s, 12H, NMe$_2$), 2.02 (t, 4H, J=7.6 Hz), 1.60 (m, 4H), 1.26 (m, 4H), 2.7-1.7 (brm, 10H, B—H). $^{11}$B NMR (160 MHz, CDCl$_3$): δ −12.8. $^{13}$C NMR (100 MHz, CDCl$_3$): δ 78.9, 58.6, 45.2, 35.3, 27.5. HRMS-ESI (m/z): Calcd. for C$_{12}$H$_{35}$B$_{10}$N$_2$ [M+H]$^+$ 315.3804. Found 315.3849. Calcd. for C$_{12}$H$_{36}$B$_{10}$N$_2$ [M+2H]$^{2+}$ 158.1938. Found 158.1966.

Synthesis of 1,12-bis(N, N, N-trimethylpropan-1-aminium)-1,12-closo-carborane di-iodide (3): Compound 3 was prepared from 15 following a similar procedure described for the preparation of 1 using a mixture of 15 (0.50 g, 1.58 mmol) and MeI (0.67 g, 4.76 mmol). The product was obtained as a white solid. Yield: 0.95 g (100%). $^1$H NMR (400 MHz, CD$_3$OD+D$_2$O drops): δ 3.22 (t, 4H, J=7.6 Hz), 3.13 (s, 18H, —NMe$_3$), 1.78 (m, 4H), 1.67 (m, 4H), 2.7-1.7 (brm, 10H, B—H). $^{11}$B NMR (128 MHz, CD$_3$OD+D$_2$O drops): δ −12.7. $^{13}$C NMR (100 MHz, CD$_3$OD+D$_2$O drops): δ 79.2, 66.2, 53.9, 34.6, 24.0. HRMS-ESI (m/z): Calcd. for C$_{14}$H$_{40}$B$_{10}$N$_2$ [M]$^{2+}$ 172.2095. Found 172.2102.

Biological Testing

Decamethonium bromide and succinylcholine chloride were purchased from Sigma Aldrich, St. Louis, MO. Rocuronium bromide, USP, was purchased from Mylar, Rockford, IL. Saline, 0.9% NaCl, USP, was purchased from Hospira, Inc. Neostigmine methylsufate, Bloxivera, USP, were purchased from Eclat Pharmaceuticals, St. Louis, MO. Iodide salts of the carborane derivatives were dissolved in the saline for testing.

Figure 5:
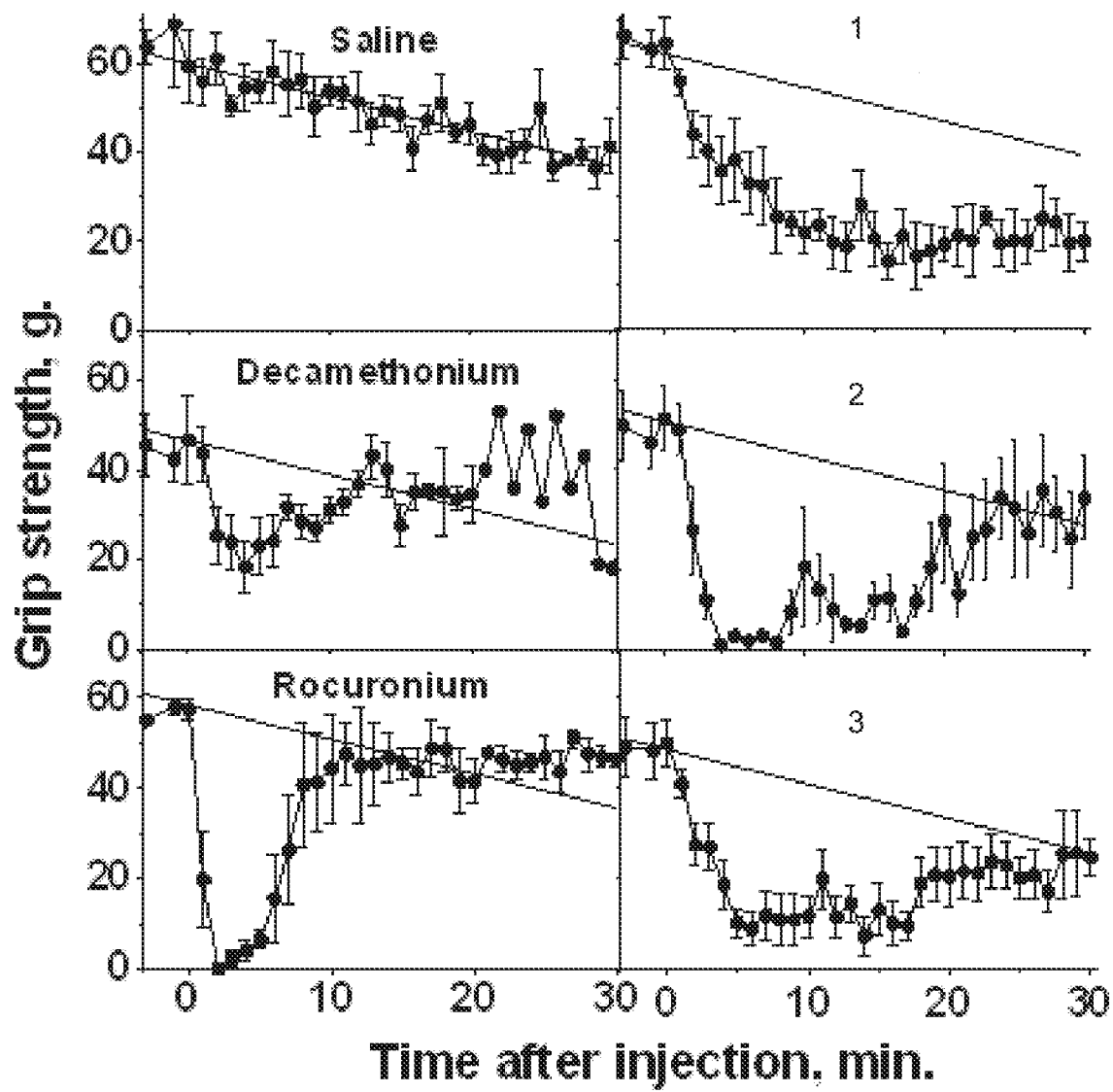
Figure 6:
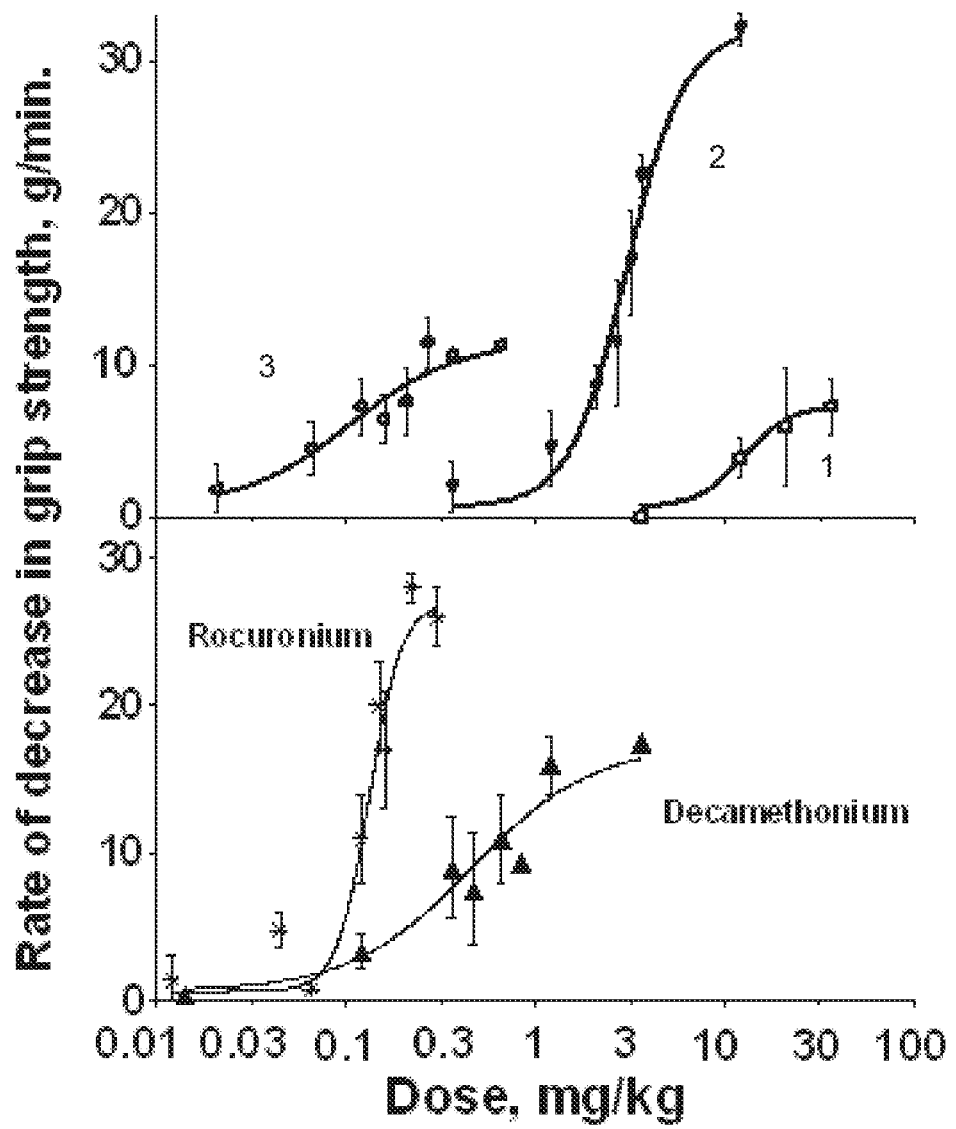
Figure 7:
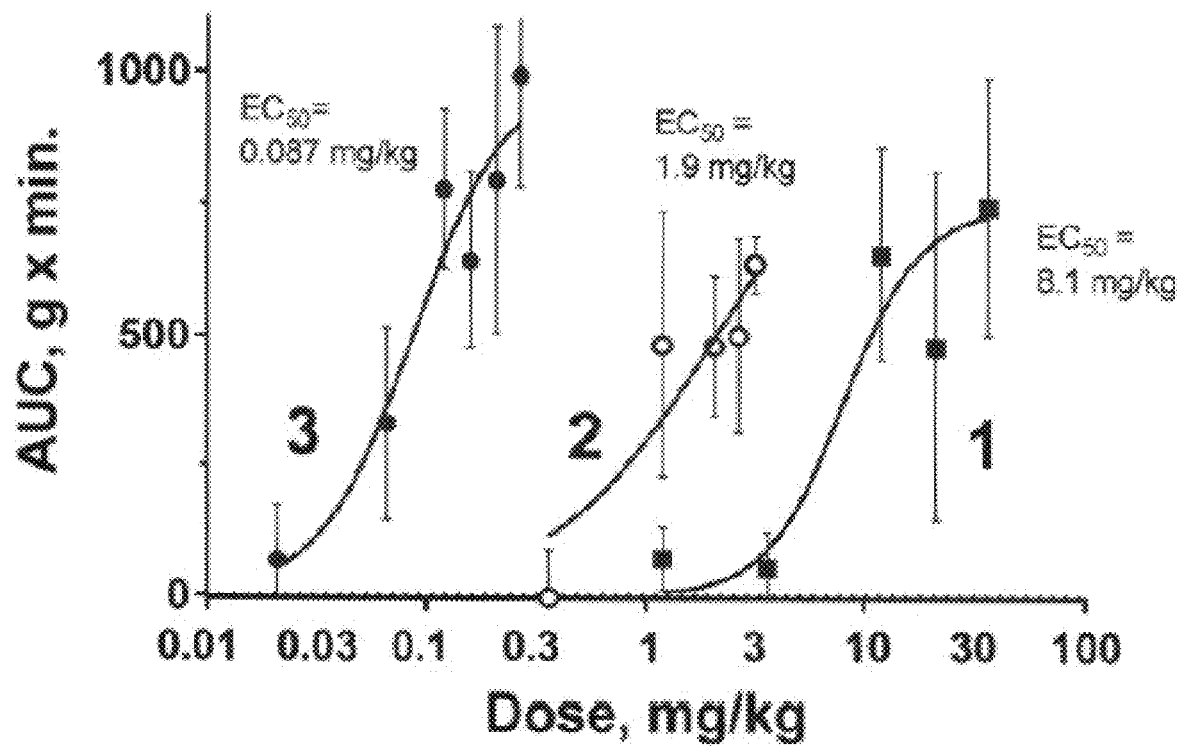

Strength Measurements in Mice: All animal experimentation protocols were approved by the University of Missouri Animal Care and Use Committee. Male Swiss Webster mice, 25-30 g, were obtained from Envigo and acclimated for 7 days. Test compounds, dissolved in saline, and saline were injected into the triceps brachii or deltoid muscles of either foreleg using a 0.3 ml disposable insulin syringe with a 30 gauge, 8 mm long needle. Mice were reused for injections in the uninjected foreleg after at least three days following the first injection. Strength measurements were performed two ways. Grip strength was measured with the grip strength test, while body strength was measured with the inverted screen test. These tests were performed one after the other at one minute intervals before and after injection. Mice were numbered and chosen for experiments from the cage by use of a random number table and the experimenters were blinded as to whether compound or saline was injected. The results are illustrated in FIGS. 5 and 6, while results of the inverted screen test are shown in FIG. 7.

The single injections began at time zero and grip strengths were measured every minute for 30 minutes. The injected doses were 0.47 mg/kg for decamethonium, n=1-7 animals, 0.22 mg/kg for rocuronium, n=5, 36 mg/kg for compound 1, n=5, 3.2 mg/kg for compound 2, n=3-5, and 0.21 mg/kg for compound 3, n=5-9. Data points are mean values f SEMs. The saline control data was fit with a linear regression line, y=0.76x+60, as shown. The neuromuscular blocker figures contain a line with the same slope as the saline control regression line for comparison.

Phrenic nerve hemi-diaphragm: All animal experimentation protocols were approved by the University of Missouri Animal Care and Use Committee. Male, Sprague-Dawley rats weighing 100-180 g were obtained from Envigo and euthanized by exposure to 4.5% isoflurane followed by exsanguination. Right and left hemi-diaphragms were removed and placed in oxygen bubbled, cold saline until use. The saline contained, in mM, 140 NaCl, 5 KCl, 1.6 CaCl$_2$·6H$_2$O, 1 NaH$_2$PO$_4$, 6 NaHCO$_3$, 5 D-glucose, 10 HEPES, pH 7.2 adjusted with 1 N NaOH, and was bubbled with 100% oxygen at 22° C. The costal cartilage of the hemi-diaphragm was secured to the floor of a 20 mL volume chamber with a metal hook and the crural end attached to a metal hook and thread leading to a force transducer (iWorx Systems, Dover, NH) and a data acquisition program (Labscribe). The phrenic nerve was introduced into a suction electrode and stimulated (pulse width=0.5 msec, supramaximal voltage=1 V) with a train of four, i.e., four stimuli in two seconds, repeated every minute. The first pulse, T1, was used as a measure of muscle strength. The results are illustrated in FIG. 7.

Figure 9A:
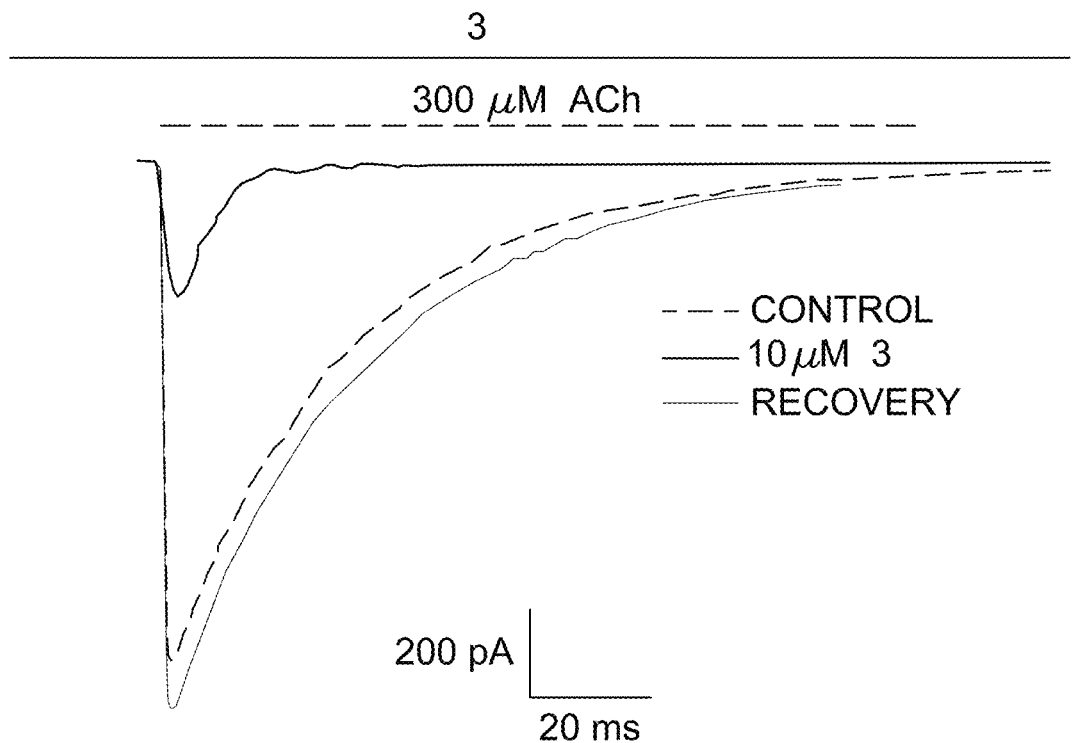
Figure 9B:
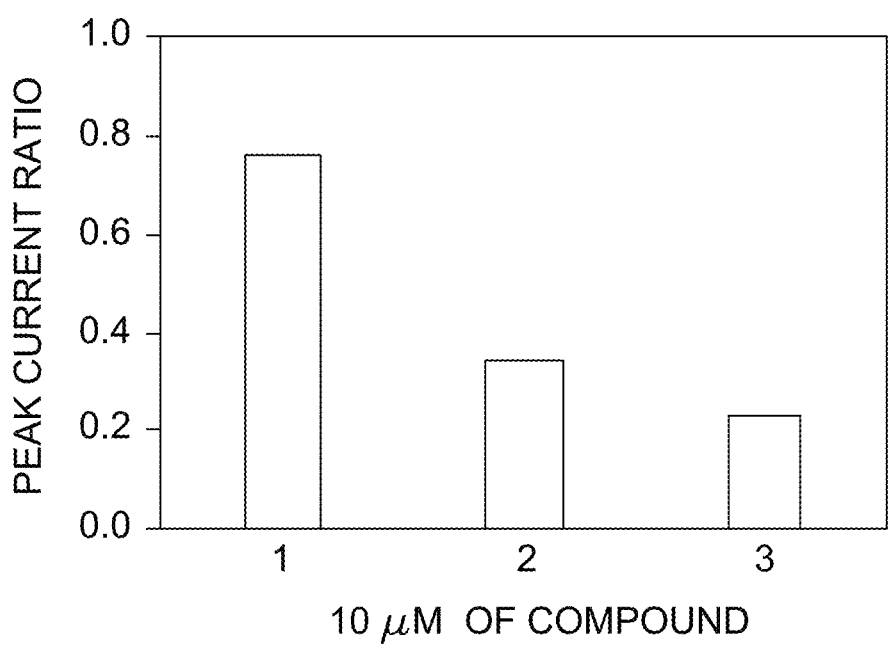

Patch clamp electrophysiology: HEK-293 cells were transfected with the cDNA for adult, human muscle acetylcholine receptors and prepared for patch clamp recording as described previously. Immediately before the experiment, the culture medium was replace with an extracellular solution (ECS) contains 150 mM NaCl, 5.6 mM KCl, 1.8 mM CaCl$_2$, 1.0 mM MgCl$_2$, and 10 mM HEPES, pH 7.3. Patch pipettes filled with a solution consisting of 140 mM KCl, 5 mM EGTA, 5 mM MgCl$_2$, and 10 mM HEPES, pH 7.3, had resistances of 3 to 4 MΩ. An outside-out patch with a seal resistance of >2 GΩ was excised from a cell and moved into position at the outflow of a HSSE-2 rapid perfusion system (ALA Scientific Instruments, Westbury, NY). The patch was rapidly and transiently perfused with 300 μM acetylcholine to activate >95% of the channels at a holding potential of −50 mV. This was the control trace; the figures show the average of 5 control traces. Subsequently, the same patch was used to test for agonist activity by the carborane compounds by switching to a reservoir containing 300-1000 μM of the compound, repeated 5 times. To test for antagonism, the patch was equilibrated with 10 μM of the compound for >3 s followed by rapid perfusion of 300 μM acetylcholine+compound. Each series of traces using a compound was followed a return to control conditions (recovery) to determine that the control current hadn't changed by more than 20%. The peak current for each series of traces was calculated. The decrease in peak current represented a combination of competitive and open-channel block by the compound. The results are illustrated in FIGS. 9A and 9B.

Data Analysis: Log concentration-response data were fit to the Hill equation $Y=X^n/(EC_{50}+X^n)$ where Y represents the response at a given drug concentration X, $EC_{50}$ is the concentration of drug yielding half-maximal response, and n is the Hill coefficient. Data were fit with GraphPad Prism version 6.00 for Windows, GraphPad Software, La Jolla California USA, and $EC_{50}$s presented as means and their 95% confidence intervals, CI, and Hill coefficients with f standard error. Statistical significance in FIG. 8 was determined by ANOVA followed by the Holm-Sidak post-test, with alpha=0.05. Each row was analyzed individually, without assuming a consistent SD, and the number of t tests was 5.

Figure 8:
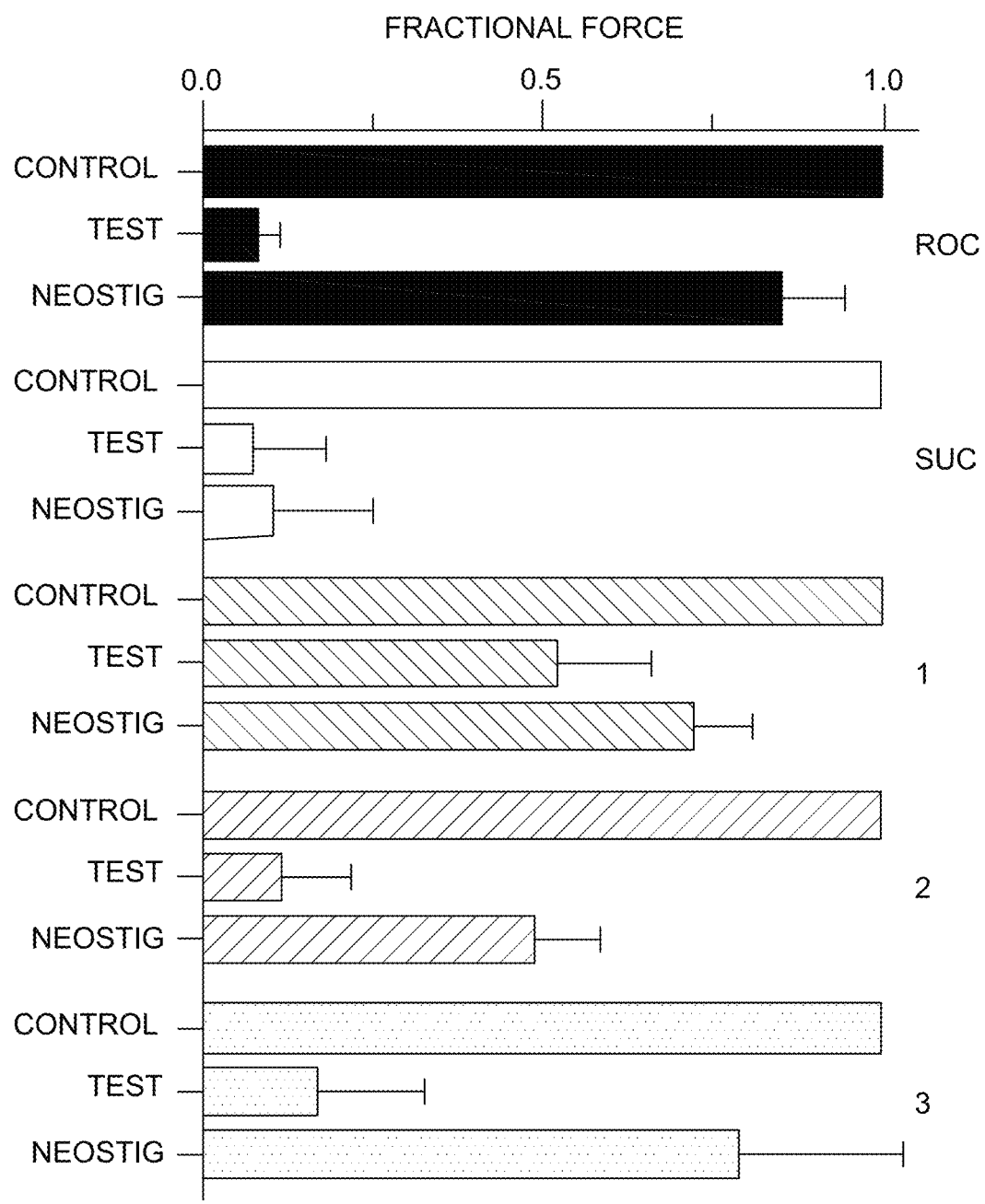

Mechanism of Action: To distinguish between mechanisms we tested whether neostigmine, an anticholinesterase that indirectly reverses the weakness caused by non-depolarizing NMBA, could reverse the muscle weakness caused by the carborane NMBA. FIG. 8 shows that in an in vitro, rat phrenic nerve, hemi-diaphragm preparation the muscle weakness caused by rocuronium 16, a non-depolarizer, was reversed by neostigmine whereas the weakness caused by succinylcholine 18, a depolarizer, was not. The muscle weaknesses caused by 1, 2 and 3 was reversed by neostigmine suggesting that these compounds are non-depolarizing NMBA. In the figure CONTROL is the force of contraction before addition of test substances, TEST is the force after the addition of test substances, NEOSTIG is the force of contraction after the addition of 1 µM neostigmine, ROC is rocuronium, and SUC is succinylcholine.

This written description uses examples to disclose the subject matter herein, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A closo-carborane compound of Formula II, III, or IV, or a pharmaceutically acceptable salt thereof:

a)

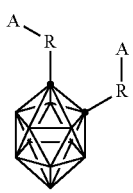

Formula II

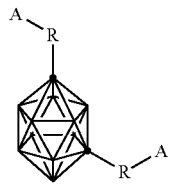

Formula III

Formula IV wherein:

are the carbon atoms in the closo-carborane;

and wherein R and A are defined by one of the following:

(i) each R is a branched or unbranched $C_2$ to $C_{10}$ alkyl group and each A is an alkyl ammonium; or (ii) each R is a branched or unbranched $C_4$ to $C_{10}$ alkyl group and each A is a cationic functional group independently selected from the group consisting of amine, ammonium, ether, alcohol, oxonium, sulfide, thiol, sulfonium, phosphane, phosphine, phosphonium, and combinations thereof, wherein at least one counter-ion is present for the cationic functional group.

2. The closo-carborane compound according to claim 1, wherein the two R groups or the two A groups are different.

* * * * *